United States Patent
Soga et al.

(10) Patent No.: US 7,209,233 B2
(45) Date of Patent: Apr. 24, 2007

(54) HIGH-SENSITIVITY REFLECTION MEASUREMENT APPARATUS

(75) Inventors: Noriaki Soga, Hachioji (JP); Hiroshi Mineo, Hachioji (JP); Kenichi Akao, Hachioji (JP)

(73) Assignee: Jasco Corporation, Hachioji-shi, Tokyo (JP)

( * ) Notice: Subject to any disclaimer, the term of this patent is extended or adjusted under 35 U.S.C. 154(b) by 99 days.

(21) Appl. No.: 11/070,785

(22) Filed: Mar. 2, 2005

(65) Prior Publication Data

US 2005/0195395 A1    Sep. 8, 2005

(30) Foreign Application Priority Data

Mar. 5, 2004    (JP)    ............................. 2004-062558

(51) Int. Cl.
    *G01J 3/30*    (2006.01)
(52) U.S. Cl. ..................................................... 356/369
(58) Field of Classification Search ..................... None
    See application file for complete search history.

(56) References Cited

U.S. PATENT DOCUMENTS

2005/0195412 A1*    9/2005    Opsal ......................... 356/630

OTHER PUBLICATIONS

Japanese Patent Abstract, Publication No. 07-120379, Published May 12, 1995 "Optical System For High-Sensitivity Reflection Measuring Apparatus".
Japanese Patent Abstract, Publication No. 09-033724, Published Feb. 7, 1997 "Reflection Type Polarizer And Spectrophotometer Using Same".

* cited by examiner

*Primary Examiner*—Tu T. Nguyen
(74) *Attorney, Agent, or Firm*—Rankin, Hill, Porter & Clark LLP

(57) ABSTRACT

A high-sensitivity reflection measurement apparatus disposed in an optical path between a light emitter and a detector of an analysis apparatus comprises an incident-side optical element, which bends the optical path of measurement light emitted from the light emitter such that the angle of incidence of the measurement light so emitted with respect to a sample surface under measurement ranges from 70° inclusive to 90° exclusive with respect to the direction perpendicular to the sample surface under measurement. The measurement light is transmitted as linearly polarized light having a desired oscillation direction, and is incident on the sample surface under measurement. Information related to the measured sample surface is obtained from light reflected from the measured sample surface when the linearly polarized light from the incident-side optical element is incident on the sample surface.

7 Claims, 11 Drawing Sheets

HIGH-SENSITIVITY REFLECTION MEASUREMENT APPARATUS

RELATED APPLICATIONS

This application claims priority based on Japanese Patent Application No. 2004-62558, filed on Mar. 5, 2004, in Japan, which is incorporated herein by reference.

BACKGROUND OF THE INVENTION

1. Field of the Invention

The present invention relates to high-sensitivity reflection measurement apparatuses, and more particularly, to the implementation of higher-sensitivity measurement with a simplified structure.

2. Prior Art

In absorbance measuring methods, which evaluate a sample by its absorption characteristic, light transmitted through the sample is detected. These methods are not suited, however, to an infrared absorption measurement of a thin film having, for example, a thickness equal to or smaller than the wavelength of infrared light. In recent years, a high-sensitivity reflection method has been known as an effective method for the absorption measurement of such thin films in infrared spectroscopic methods.

In the high-sensitivity reflection method, light is incident on a sample at a large incident angle, and light reflected from the sample is detected to determine the optical absorption state of the sample surface under measurement. High-sensitivity reflection measurement apparatuses employing this method have also been developed (disclosed, for example, in Japanese Unexamined Patent Application Publication No. Hei-7-120379).

Even in such high-sensitivity reflection measurement apparatuses, further improvement of measurement sensitivity has been demanded. Although higher sensitivity with a simple structure has been strongly demanded, there has been conventionally no appropriate technology to implement it.

SUMMARY OF THE INVENTION

The present invention has been made to solve the foregoing problem. Accordingly, it is an object of the present invention to provide a high-sensitivity reflection measurement apparatus capable of higher sensitivity measurements with a simple structure.

<Wedge-Shaped Polarizer>

A high-sensitivity reflection measurement apparatus according to the present invention is disposed in an optical path between a light emitter and a detector of an analysis apparatus, the high-sensitivity reflection measurement apparatus comprises an incident-side optical element. The incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement. In the high-sensitivity reflection measurement apparatus, information related to the sample surface under measurement is obtained according to light reflected from the sample surface under measurement when the linearly polarized light from the incident-side optical element is incident on the sample surface under measurement.

In the high-sensitivity reflection measurement apparatus according to the present invention, it is preferable that the incident-side optical element is a wedge-shaped optical element having a wire grid polarizer.

The wedge-shaped optical element having a wire grid polarizer has transmittance with respect to the measurement light and a higher refractive index than an atmosphere in the optical path of the measurement light. And the wedge-shaped optical element having a wire grid polarizer is a wedge-shaped optical element having a wire grid polarizer made by providing a wire grid on a wedge-shaped measurement-light transmission substrate for bending the optical path of the measurement light emitted from the light emitter such that the angle of incidence of the measurement light with respect to the sample surface under measurement, after passing through the incident-side optical element, is a desired angle ranging from 70 degrees inclusive to 90 degrees exclusive.

In the high-sensitivity reflection measurement apparatus according to the present invention, it is preferable that the high-sensitivity reflection measurement apparatus further comprises: a wedge-shaped outgoing-side optical element; a casing; and a sample placement section. The incident-side optical element makes the measurement light incident on the sample surface under measurement of a sample placed at the sample placement section. And the outgoing-side optical element takes out the light reflected from the sample surface under measurement.

The wedge-shaped outgoing-side optical element bends the optical path of the light reflected from the sample surface under measurement such that the optical path of the light reflected from the sample surface under measurement matches an optical path to the detector when the light reflected from the sample surface under measurement is transmitted.

The casing accommodates at least the incident-side optical element and the outgoing-side optical element.

The sample placement section is provided on the casing, sets the sample.

<Light Limiter>

In the high-sensitivity reflection measurement apparatus according to the present invention, it is preferable that the high-sensitivity reflection measurement apparatus further comprises: a sample mask; and a light-shielding plate.

The sample mask has an opening limits the sample surface under measurement.

The light-shielding plate is disposed in the direction perpendicular to the sample surface under measurement, at a certain gap with respect to the sample surface under measurement, the gap being equal to a distance determined according to the size of the opening of the sample mask. The light-shielding plate takes out reflected light having reflection points of the measurement light on the sample surface under measurement limited by the opening of the sample mask and having an angle of incidence ranging from 70 degrees inclusive to 90 degrees exclusive at the reflection points, through the gap with respect to the sample surface under measurement, and blocks other unnecessary light.

In the high-sensitivity reflection measurement apparatus according to the present invention, it is preferable that the high-sensitivity reflection measurement apparatus further comprises: a spacer; and a moving unit.

The spacer is disposed at the side opposite the sample surface under measurement, of the sample mask and has a thickness determined according to the size of the opening of the sample mask.

The moving unit moves and holds the light-shielding plate at any position in the direction perpendicular to the sample surface under measurement.

When the spacer for the sample mask is abutted against the light-shielding plate to place the sample mask and the light-shielding plate in position, the moving unit relatively moves the light-shielding plate by a distance corresponding to the thickness of the spacer in a direction in which the gap with respect to the sample surface under measurement increases to make the gap between the sample-surface under measurement and the light-shielding plate equal to the distance determined according to the size of the opening of the sample mask.

<Sample Shuttle>

In the high-sensitivity reflection measurement apparatus according to the present invention, it is preferable that the high-sensitivity reflection measurement apparatus further comprises a sample shuttle. The sample shuttle alternately performs a sample measurement with a sample under measurement and a reference measurement with a reference sample. The sample shuttle comprises: a sample holder; a driver; and controller.

The sample holder holds the sample under measurement and the reference sample.

The sample holder is provided so as to reciprocate freely in order to alternately place the sample under measurement and the reference sample in the optical path of the measurement light.

The driver reciprocates the sample holder to alternately place the sample under measurement and the reference sample in the optical path of the measurement light.

The controller controls the reciprocating movement of the sample holder driven by the driver. And the controller makes the driver alternately place the sample under measurement and the reference sample held by the sample holder in the optical path of the measurement light according to a predetermined measurement sequence such that the measurement light is alternately incident on the sample under measurement and the reference sample to alternately perform the sample measurement and the reference measurement.

<Optical-Element Shuttle>

In the high-sensitivity reflection measurement apparatus according to the present invention, it is preferable that the high-sensitivity reflection measurement apparatus further comprises an optical-element shuttle for alternately performing a sample measurement with p-polarized light and a reference measurement with s-polarized light, for an identical sample under measurement. The incident-side optical element comprises: a p-polarizer for generating the p-polarized light; and an s-polarizer for generating the s-polarized light. The optical-element shuttle comprises: an optical-element holder; a driver; and a controller. The optical-element holder holds the p-polarizer and the s-polarizer. The optical-element holder is provided so as to reciprocate freely in order to alternately place the p-polarizer and the s-polarizer in the optical path of the measurement light. The driver reciprocates the optical-element holder to alternately place the p-polarizer and the s-polarizer in the optical path of the measurement light. The controller controls the reciprocating movement of the optical-element holder driven by the driver. The controller makes the driver alternately place the p-polarizer and the s-polarizer held by the optical-element holder in the optical path of the measurement light according to a predetermined measurement sequence such that the p-polarized light and the s-polarized light are alternately incident on the identical sample under measurement to alternately perform the sample measurement and the reference measurement.

DESCRIPTION OF THE PREFERRED EMBODIMENT

Figure 1A:
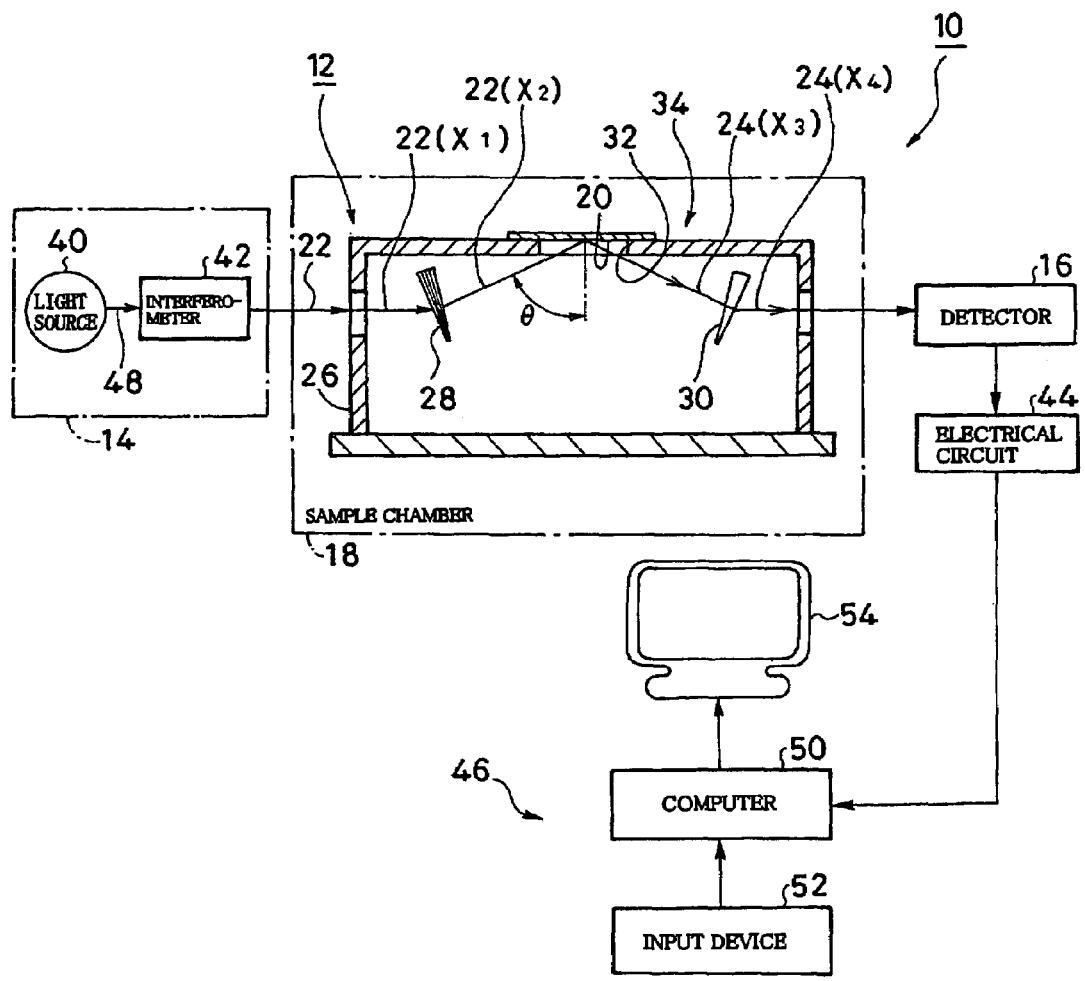
FIG. 1A and FIG. 1B are views showing an outline structure of an FTIR apparatus which employs a high-sensitivity reflection measurement apparatus according to an embodiment of the present invention.

Preferred embodiments of the present invention will be described below by referring to the drawings.

First Embodiment (Wedge-shaped Polarizer)

In the present embodiment, a wedge-shaped polarizer suited to a high-sensitivity reflection measurement apparatus will be described.

Figure 1B:
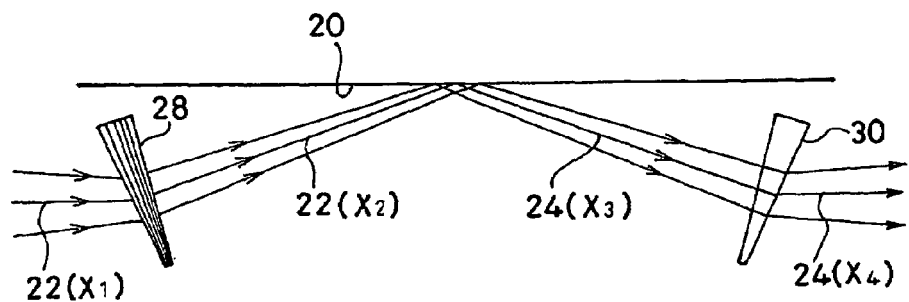

FIG. 1 shows an outline structure of an FTIR apparatus according to an embodiment of the present invention.

An FTIR (Fourier Transform Infrared Spectroscopy) apparatus (analysis apparatus) 10 shown in the figure includes a high-sensitivity reflection measurement apparatus 12 for implementing a high-sensitivity reflection measurement method in an infrared region.

The high-sensitivity reflection measurement apparatus 12 is provided detachably in a sample chamber 18 between a light emitter 14 and a detector 16 in the FTIR apparatus 10.

The high-sensitivity reflection measurement apparatus 12 is used to obtain information related to a sample surface 20 under measurement of, for example, a thin film (sample) based on light 24 reflected from the sample surface 20 under measurement with the angle of incidence θ of measurement light 22 on the sample surface 20 under measurement with respect to the direction perpendicular to the sample surface 20 under measurement being set to 70 degrees (inclusive) to 90 degrees (exclusive).

The high-sensitivity reflection measurement apparatus 12 includes a casing 26, a wedge-shaped window (incident-side optical element) 28 having a wire grid polarizer, and a wedge-shaped window plate (wedge-shaped, outgoing-side optical element) 30.

The wedge-shaped window 28 having the wire grid polarizer and the wedge-shaped window plate 30 are disposed in the casing 26. At an upper part of the casing 26, a sample placement section 34 having an opening 32 is provided. The sample is disposed horizontally on the casing 26 such that the sample surface 20 under measurement is located at the opening 32 of the sample placement section 34.

The wedge-shaped window 28 having the wire grid polarizer is made by integrating an infrared-transmitting wedge-shaped window substrate for bending infrared light, and a wire-grid polarizer. The wedge-shaped window 28 having the wire grid polarizer bends an optical path $X_1$ of the measurement light 22 output from the light emitter 14 to an optical path $X_2$ such that the angle of incidence θ of the measurement light 22 on the sample surface 20 is set to a desired angle in a range of 70 degrees (inclusive) to 90 degrees (exclusive), and transmits the measurement light as p-polarized light to be incident on the sample surface 20 under measurement.

The wedge-shaped window plate 30 bends an optical path $X_3$ of the light 24 reflected from the sample surface 20 under measurement to an optical path $X_4$ toward the detector 16 when the light 24 reflected from the sample surface 20 under measurement is transmitted there through.

In this way, the measurement light 22 output from the light emitter 14 is incident, through the wedge-shaped window 28 having the wire grid polarizer, on the surface 20 under measurement of the sample disposed on the sample placement section 34, and the light 24 reflected from the sample surface 20 under measurement passes through the wedge-shaped window plate 30 to the detector 16 in the next stage.

The wedge-shaped window 28 having the wire grid polarizer will be described below in detail.

The wedge-shaped window 28 having the wire grid polarizer is made by providing a wire grid on a wedge-shaped infrared-transparent substrate. The wedge-shaped infrared-transparent substrate has transparency for the measurement light 22, which is in the infrared region, and also has a higher refractive index than the atmosphere in the optical path of the measurement light 22. Therefore, even though the wedge-shaped window 28 having the wire grid polarizer is just one optical element, it bends the infrared measurement light by a large amount and also generates p-polarized light.

As a result, in the present embodiment, since the wedge-shaped window 28 having the wire grid polarizer is used as an optical element of the high-sensitivity reflection measurement apparatus, a larger angle of incidence is obtained with respect to the sample surface 20 under measurement than with other optical elements, and measurement is performed with higher sensitivity. Also, in the present embodiment, the structure of the apparatus is simpler and more robust than when other optical elements are used. Further, in the present embodiment, more highly efficient, more stable measurement is performed than when other optical elements are used.

In the present embodiment, the FTIR apparatus 10 has a light source 40 and an interferometer 42, as the light emitter 14. The FTIR apparatus 10 also has an electrical circuit 44 and a computer system 46.

The light source 40 emits infrared light 48. The infrared light 48 emitted from the light source 40 is changed to interference light falling in the infrared region, by the interferometer 42. This light is used as the measurement light 22.

The detector 16 converts the reflected light 24 having the optical absorption information of the sample surface 20 under measurement to an electrical signal. The electrical circuit 44 samples the electrical signal sent from the detector 16 to convert the analog signal to a digital signal.

The computer system 46 includes a computer 50, an input device 52, a display unit 54, and other components. The computer 50 adds up interferograms sent from the electrical circuit 44, and applies a Fourier transform to the result to obtain an infrared spectrum, according to a measurement sequence specified by the input device 52 in the computer 50. The computer 50 also displays the obtained infrared spectrum on the display unit 54.

The function of an incident-side optical element suited to the high-sensitivity reflection measurement apparatus according to the present embodiment will be described below in detail.

Compared with other measurement apparatuses, there is more demand for high-sensitivity reflection measurement apparatuses to have a high optical efficiency to obtain signals related to minute samples and to have high sensitivity. There are also demands to have simple structures because high-sensitivity reflection measurement apparatuses tend to have complicated structures and to have large sizes due to the arrangement of optical elements. It is desirable for high-sensitivity reflection measurement apparatuses to satisfy these demands.

In the high-sensitivity reflection measurement method, when light is incident on a sample at a large angle of incidence, sensitivity increases. If the light is p-polarized light, the sensitivity is further increased.

Among the various types and combinations of optical-path bending devices and polarizers, the inventors have found that the wedge-shaped window 28 having the wire grid polarizer is very effective for high-sensitivity reflection measurement apparatuses, not only for achieving higher measurement sensitivity but also for improving the main characteristics.

The measurement light 22 (optical path $X_1$) emitted from the interferometer 42, at the left-hand part of the figure, enters the high-sensitivity reflection measurement apparatus 12, and is then incident on the wedge-shaped window 28 having the wire grid polarizer. The wedge-shaped window 28 having the wire grid polarizer bends the optical path of the measurement light 22 from the direction (optical path $X_1$) toward the right in the figure to the direction (optical path $X_2$) toward the upper right in the figure due to the refraction effect. At the same time, the measurement light 22 is changed to p-polarized light due to the effect of the wire grid polarizer. This p-polarized light is incident on the sample surface 20 under measurement at as a large angle of incidence, such as 70 degrees (inclusive) to 90 degrees (exclusive). The light 24 reflected from the sample surface 20 under measurement is incident on the wedge-shaped optical element 30. The wedge-shaped optical element 30 changes the optical path from the direction (optical path $X_3$) toward the lower right in the figure to the direction (optical path $X_4$) toward the right in the figure, and the reflected light 24 goes out of the high-sensitivity reflection measurement apparatus 12. In the subsequent stage, the reflected light 24 (optical path $X_4$) output from the high-sensitivity reflection measurement apparatus 12 is detected to determine the optical absorption state on the sample surface 20 under measurement.

In the present embodiment, as described above, since the wedge-shaped window 28 having the wire grid polarizer is used as an incident-side optical element, a larger angle of incidence and a higher-sensitivity measurement are obtained than with other optical elements. The high-sensitivity reflection measurement apparatus has a simple and robust structure, and performs highly-efficient stable measurements.

The following optical elements can be used in high-sensitivity reflection measurement apparatuses to obtain a large angle of incidence and linearly polarized light. The wedge-shaped window 28 having the wire grid polarizer is, however, more suited in terms of the points described below.

Figure 2A:
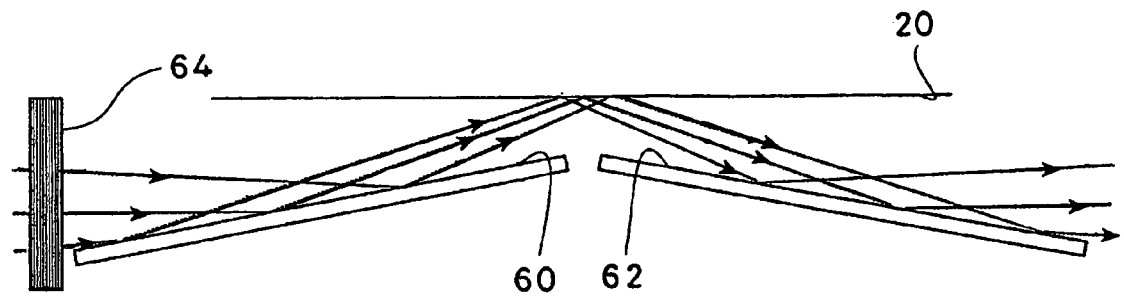
FIG. 2A, FIG. 2B, and FIG. 2C show example optical-system components which can be used in the high-sensitivity reflection measurement apparatus.

Mirrors 60 and 62 may be used in a high-sensitivity reflection apparatus as shown in FIG. 2A to obtain a large angle of incidence. In this case, a rectangular wire grid polarizer 64 may be used. However, to obtain a large angle of incidence, the mirrors 60 and 62 need to be large, their arrangement is difficult, and their adjustment is also difficult.

Figure 2B:
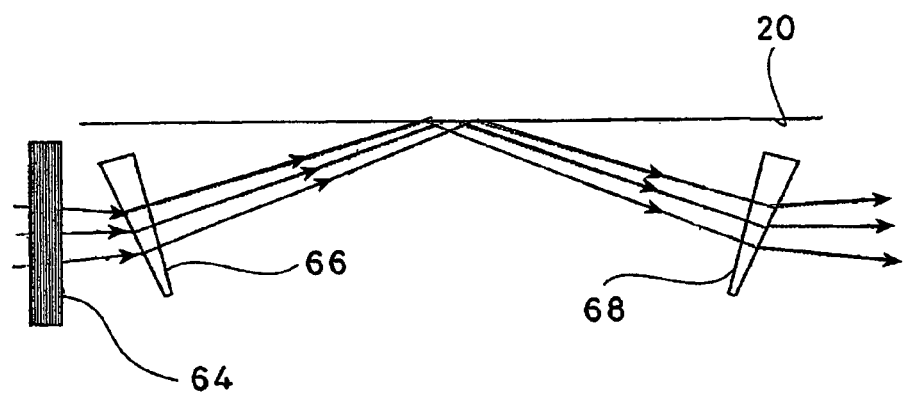

In another case, wedge-shaped optical elements 66 and 68 may be used in a high-sensitivity reflection apparatus as shown in FIG. 2B to obtain a large angle of incidence. In this case, a rectangular wire grid polarizer 64 may be used. However, since three optical elements having higher refractive indexes than air, namely, the two wedge-shaped optical elements 66 and 68 and the rectangular wire grid polarizer 64, are used, a large reflection loss occurs at the optical elements, thus reducing light-use efficiency.

Figure 2C:
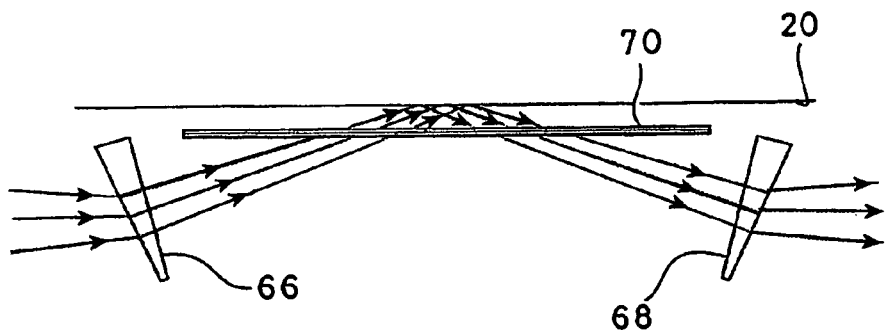

In still another case, the wedge-shaped optical elements 66 and 68 may be used in a high-sensitivity reflection apparatus as shown in FIG. 2C to obtain a large angle of incidence. In this case, a Brewster's-angle-incidence polarizer 70 may be used. The Brewster's-angle-incidence polarizer 70 includes a substrate having a very high refractive index, and changes measurement light incident thereon at Brewster's angle to p-polarized transmission light. The polarizer 70 is large. In addition, since it needs to be thin, it is fragile.

In contrast, since the wedge-shaped window 28 having the wire grid polarizer is used as an incident-side optical element in the present embodiment, a larger angle of incidence is obtained compared with the apparatuses shown in FIG. 2A to FIG. 2C. Therefore, higher-sensitivity measurements can be performed in the present embodiment. In addition, the high-sensitivity reflection measurement apparatus according to the present embodiment has a simple and robust structure, and performs highly-efficient stable measurements.

The present invention is not limited to the structure described above, and can be variously modified within the scope of the gist of the present invention.

In the present invention, for example, it is also preferable that the following light limiter (second embodiment) or the following shuttles (third embodiment) be added.

It is especially preferred that the light limiter according to the second embodiment and the shuttles according to the third embodiment be used in a high-sensitivity reflection measurement apparatus having the wedge-shaped window 28 having the wire grid polarizer, due to the same reason as for the first embodiment. The light limiter and the shuttles can also be used for high-sensitivity reflection measurement apparatuses using the optical elements shown in FIG. 2A, FIG. 2B, and FIG. 2C.

Second Embodiment (Light Limiter)

In the present embodiment, a light limiter suited to a high-sensitivity reflection measurement apparatus will be described. The same numerals as those used in the first embodiment plus 100 are assigned to portions corresponding to those shown in the first embodiment. A description thereof is omitted.

Figure 3A:
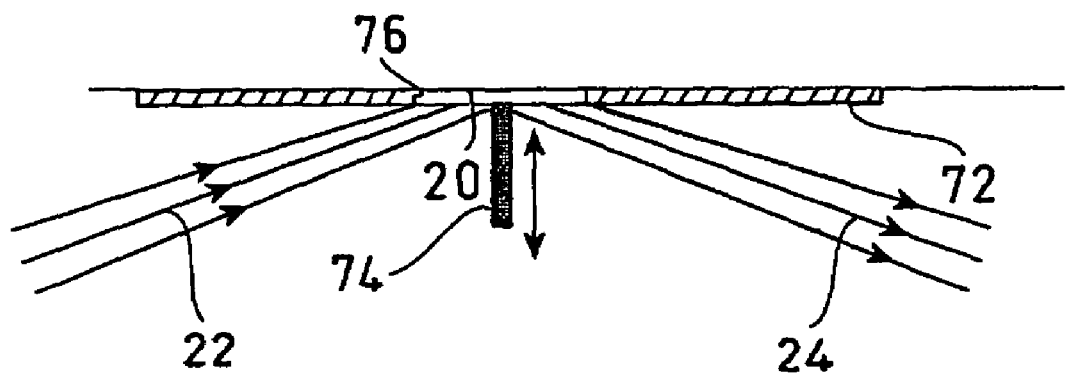
FIG. 3A and FIG. 3B are views showing an outline structure of a light limiter suited to a high-sensitivity reflection measurement apparatus according to another embodiment of the present invention.
Figure 3B:
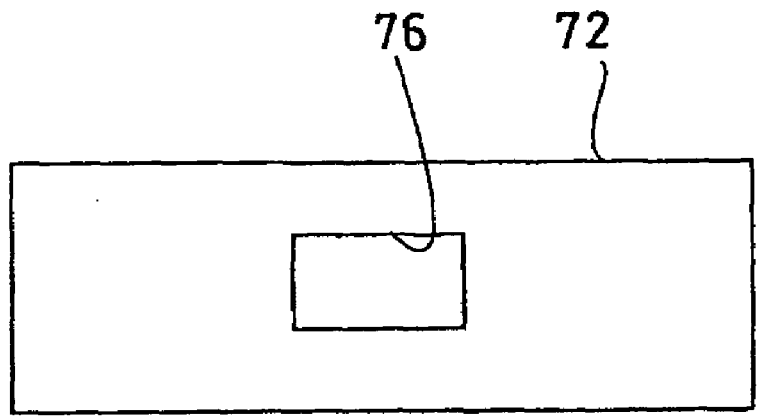

FIG. 3A and FIG. 3B show an outline structure of the light limiter according to the second embodiment. FIG. 3A is a side view of the light limiter, and FIG. 3B is a rear view of an opening plate (sample mask).

The light limiter shown in FIG. 3A and FIG. 3B includes an opening plate (sample mask) 72 and a light-shielding plate 74. The sample surface 20 under measurement is placed at a surface of the opening plate 72. The opening plate 72 has an opening 76 for limiting the sample surface 20 under measurement. The light-shielding plate 74 is disposed in the direction perpendicular to the sample surface 20 under measurement at a certain gap from the sample surface 20 under measurement, the gap being equal to a distance specified according to the size of the opening 76 of the opening plate 72.

To change the size of the measurement area of the sample surface 20 under measurement, an opening plate 72 having an opening 76 with a different size is used. The light-shielding plate 74 is moved up or down in the figure according to the size of the opening 76 of the opening plate 72 to adjust the position of the light-shielding plate 74 with respect to the sample surface 20 under measurement.

The light-shielding plate 74 takes out, through the gap with respect to the sample surface 20 under measurement, the reflected light 24 having reflection points of the measurement light 22 limited by the opening 76 of the opening plate 72 on the measurement area, and having the angle of incidence ranging from 70 degrees (inclusive) to 90 degrees (exclusive) at the reflection points on the measurement area, and blocks other unnecessary light.

In the present embodiment, anti-reflection treatment is applied to the rear surface of the opening plate 72, which is the side opposite the side contacting the sample surface 20 under measurement.

Figure 4A:
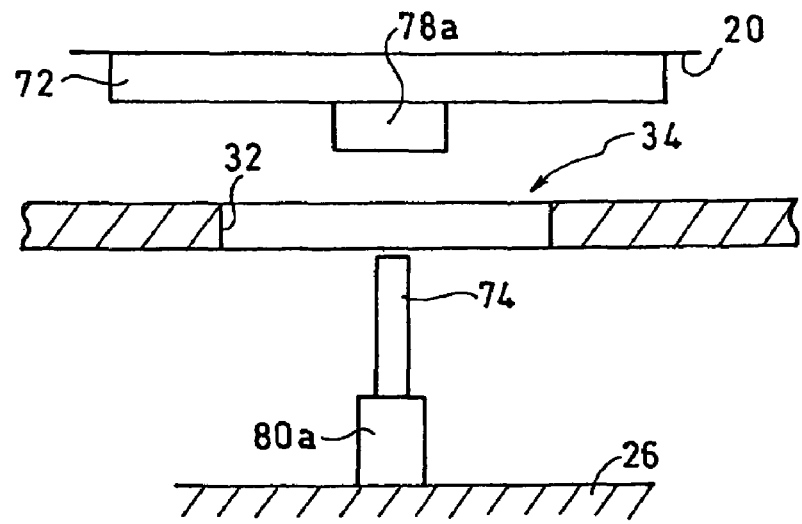
FIG. 4A, FIG. 4B, and FIG. 4C are views showing a specific structure of the light limiter shown in FIG. 3A and FIG. 3B.
Figure 4B:
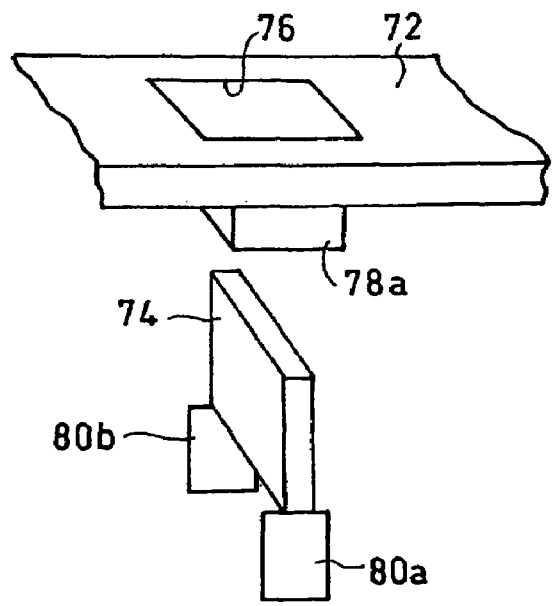
Figure 4C:
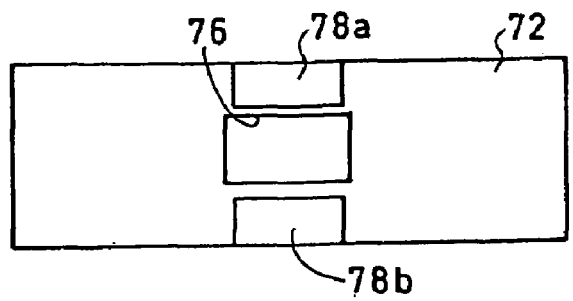

FIG. 4A to FIG. 4C show a specific structure of an automatic light limiter. The automatic light limiter is formed of the light limiter shown in FIG. 3, light-shielding-plate holders (spacers) 78a and 78b, and moving units 80a and 80b. FIG. 4A is a side view of the automatic light limiter, on which a sample is set. FIG. 4B is a perspective view of the automatic light limiter without a sample. FIG. 4C is a rear view of the opening plate of the automatic light limiter.

The light-shielding-plate holders 78a and 78b are provided at the rear surface of the opening plate 72, which is the side opposite the side contacting the sample surface 20, and have a thickness specified according to the size of an opening 76 of the opening plate 72.

The moving units 80a and 80b are formed of springs or other elements, and are provided so as to allow movement of the light-shielding plate 74 in the direction perpendicular to the sample surface 20 under measurement. In the present embodiment, one end of each spring is connected to the casing 26, and the other end of the spring is connected to the lower surface of the light-shielding plate 74. The spring extends and contracts in the up and down direction as the light-shielding plate 74 moves up and down.

When the lower surfaces of the light-shielding-plate holders 78a and 78b of the opening plate 72 are a butted against the upper surface of the light-shielding plate 74, and the opening plate 72 is placed in position, the light-shielding plate 74 is moved by the moving units 80a and 80b by a distance corresponding to the thickness of the light-shielding-plate holders 78a and 78b in the direction in which the gap with respect to the sample surface 20 under measurement increases. As a result, the gap between the sample surface 20 under measurement and the light-shielding plate 74 is automatically set to the distance determined according to the size of the opening 76 of the opening plate 72. The position of the light-shielding plate 74 can be thus easily changed. In the present embodiment, since the light-shielding plate 74 always removes unnecessary light even with an opening plate 72 having a different-size opening 76, the absorption level of a sample under measurement is measured with more reliability irrespective of the size of the opening 76 of the opening plate 72.

The function of a light limiter suited to the high-sensitivity reflection measurement apparatus according to the present embodiment will be described below in more detail.

In the high-sensitively reflection measurement method, removing unnecessary light is important because it largely affects the performance of the apparatus. In the present invention, since a sample surface under measurement is illuminated with light at a large angle of incidence, the size of the opening of a sample base is changed to change the size of the measurement area. Unnecessary light needs to be removed optimally according to the size of the opening.

To change the size of the measurement area, a plate having a different-size opening may be used. In this case, anti-reflection treatment may be applied to the rear surface of the opening plate to reduce unnecessary light. In the anti-reflection treatment, however, it was found that unnecessary light could not be sufficiently removed. Light reflected from the rear surface of the opening plate affected the performance of the apparatus.

Light reflected from the rear surface of the opening plate is reduced more to further remove unnecessary light even with different-size openings, thus achieving the present invention.

More specifically, in the present invention, when the size of the opening of the opening plate is changed, the shape of the light limiter is changed according to the changed size of the opening to remove unnecessary light even for the opening with the changed size.

In the present embodiment, the opening plate 72, the light-shielding plate 74 which moves up and down according to the size of the opening 76, the light-shielding-plate holders 78a and 78b, and the moving unit 80a and 80b are provided. The position of the light-shielding plate 74 is changed by changing the thickness of the light-shielding-plate holders 78a and 78b provided for the opening plate 72.

Figure 5A:
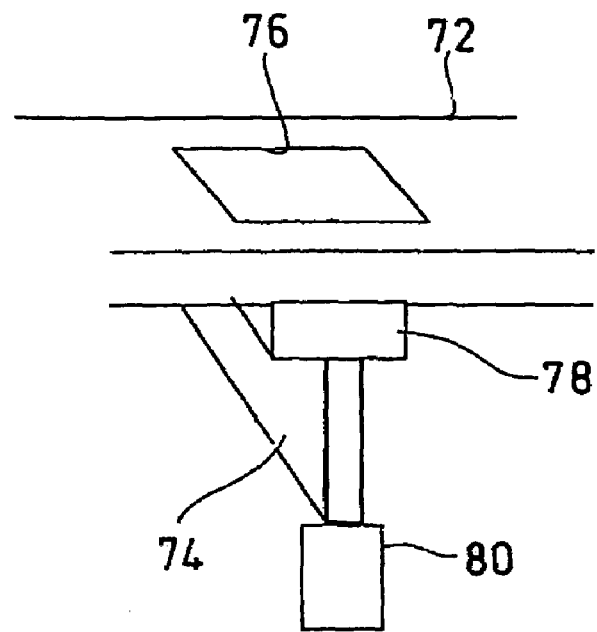
FIG. 5A and FIG. 5B are views showing a measurement configuration of the light limiter shown in FIG. 4A, FIG. 4B, and FIG. 4C.
Figure 5B:
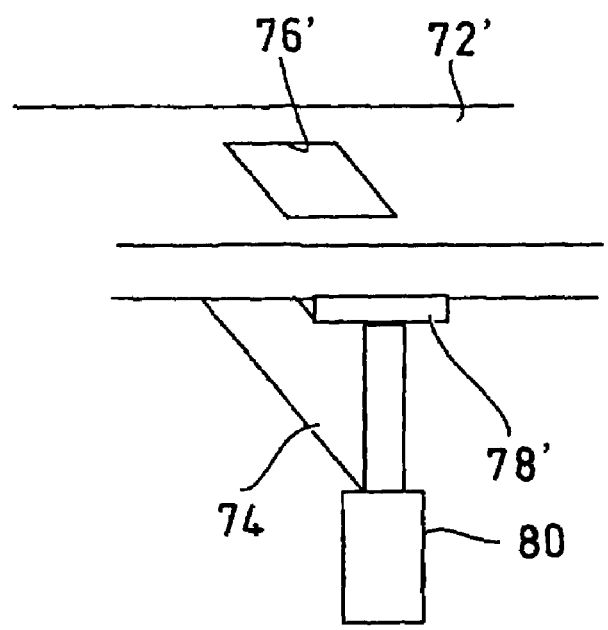

The present embodiment will be described by referring to FIG. 5. FIG. 5A shows the position of the light-shielding plate 74 obtained when an opening plate 72 having a large opening 76 is used. FIG. 5B shows the position of the light-shielding plate 74 obtained when an opening plate 72' having a small opening 76' is used.

The light-shielding plate 74 has identical dimensions both when the opening plate 72 having the large opening 76 is used and when the opening plate 72' having the small opening 76' is used.

In contrast, light-shielding-plate holders have different thicknesses corresponding to the sizes of the openings. A thick light-shielding-plate holder 78 is used for the opening plate 72 having the large opening 76. A thin light-shielding-plate holder 78' is used for the opening plate 72' having the small opening 76'.

When the opening plate 72 is placed in position, since the moving unit 80, such as a spring, moves the light-shielding plate 74 up, the light-shielding-plate holder 78 abuts against the light shielding plate 74, as shown in FIG. 5A. When the opening plate 72' is placed in position, since the moving unit 80 moves the light-shielding plate 74 up, the light-shielding-plate holder 78' abuts against the light shielding plate 74, as shown in FIG. 5B. In this way, irrespective of the sizes of the openings 76 and 76', the light-shielding-plate holders 78 and 78' abut against the light shielding plate 74 in both cases.

When the opening plate 72 having the large opening 76 is used, the light-shielding plate 74 is positioned lower with respect to the sample surface under measurement by the thick light-shielding-plate holder 78 than when the opening plate 72' having the small opening 76' is used. When the opening plate 72' having the small opening 76' is used, the light-shielding plate 74 is positioned higher with respect to the sample surface under measurement by the thin light-shielding-plate holder 78' than when the opening plate 72 having the large opening 76 is used.

Therefore, since the gap between the sample surface under measurement and the light-shielding plate 74 automatically corresponds to the sizes of the openings 76 and 76' in the two above-described cases, unnecessary light is always removed by the light-shielding plate 74 even if the openings having different sizes are used.

Figure 6A:
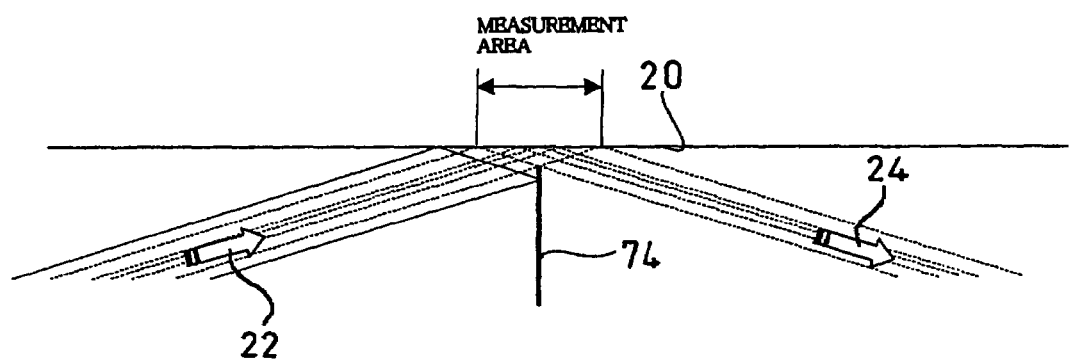
FIG. 6A and FIG. 6B are views showing a measurement function of the light limiter shown in FIG. 4A, FIG. 4B, and FIG. 4C.
Figure 6B:
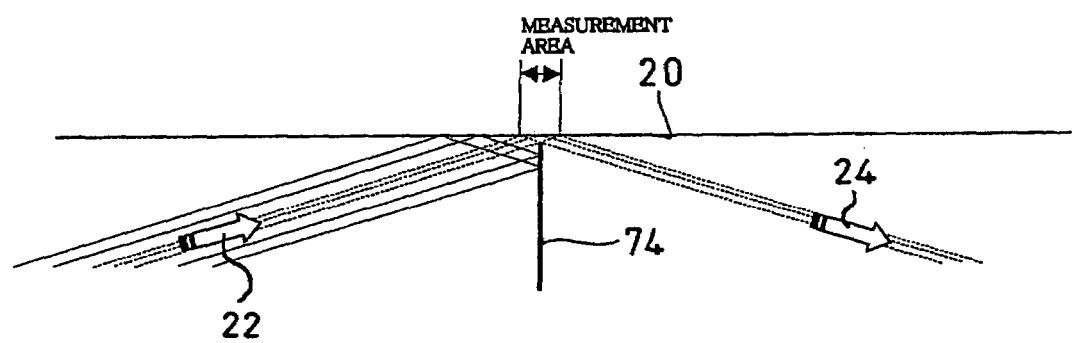

This issue will be further described by referring to FIG. 6A and FIG. 6B. FIG. 6A shows measurement with the opening plate 72 having the large opening 76. FIG. 6B shows measurement with the opening plate 72' having the small opening 76'.

As shown in FIG. 6A, when the opening plate 72 having the large opening 76 is used, the gap between the sample surface 20 under measurement and the light-shielding plate 74 is larger and an area (indicated as a measurement area in the figure) where light is reflected from the sample surface 20 under measurement is wider than in FIG. 6B. As shown in FIG. 6B, when the opening plate 72' having the small opening 76' is used, the gap between the sample surface 20 under measurement and the light-shielding plate 74 is smaller and an area (indicated as a measurement area in the figure) where light is reflected from the sample surface 20 under measurement is narrower than in FIG. 6A.

The light-shielding plate 74 takes out, through the gap with respect to the sample surface 20 under measurement, the reflected light 24 having reflection points of the measurement light 22 limited by the opening of the opening plate on the measurement area, and having the angle of incidence ranging from 70 degrees (inclusive) to 90 degrees (exclusive) at the reflection points on the measurement area, and blocks other unnecessary light.

Since the size of the gap is automatically adjusted correspondingly to the size of the opening used, an appropriate gap is automatically set even with a different-size opening. Therefore, the absorption level of a sample under measurement can be measured with reliability irrespective of the size of the opening because unnecessary light is always removed.

Third Embodiment (Sample Shuttle and Optical-Element Shuttle)

A sample shuttle suited to a high-sensitivity reflection measurement apparatus will be described next.

The high-sensitivity reflection measurement method measures a thin film placed on a metal surface with high sensitivity. Since the sample under measurement is a thin film, a very small peak is obtained in many cases. To obtain the spectrum of a sample having a small peak, a method in which adding up is performed and the peak is separated from noise can be considered.

With single-beam spectroscopes such as FTIR apparatuses, a reference measurement and a sample measurement are performed at different times, and as a result, an artifact may occur due to baseline bending or gas imbalance in the air. Such an artifact may affect small-peak analysis.

If an artifact occurs in a high-sensitivity reflection measurement, it is generally thought that data is compensated by a data processor or block accumulation is artificially performed, both of which are complicated operations.

In the present invention, a shuttle for alternately performing a reference measurement and a sample measurement is provided at a sample placement section of a high-sensitivity reflection apparatus to perform block accumulation to remove any artifact. In the present embodiment, as a shuttle for the high-sensitivity reflection measurement apparatus, a sample shuttle for switching between a reference sample and a sample to be measured, or an optical-element shuttle for switching between s-polarized light and p-polarized light can be used.

<Sample Shuttle>

In the present embodiment, a sample shuttle electrically driven for alternately placing a reference sample and a sample under measurement in an optical path is used. The sample shuttle is operated in synchronization with a measurement sequence to switch between the reference sample and the sample under measurement and to perform block accumulation without breaking sample-chamber sealing.

Figure 7A:
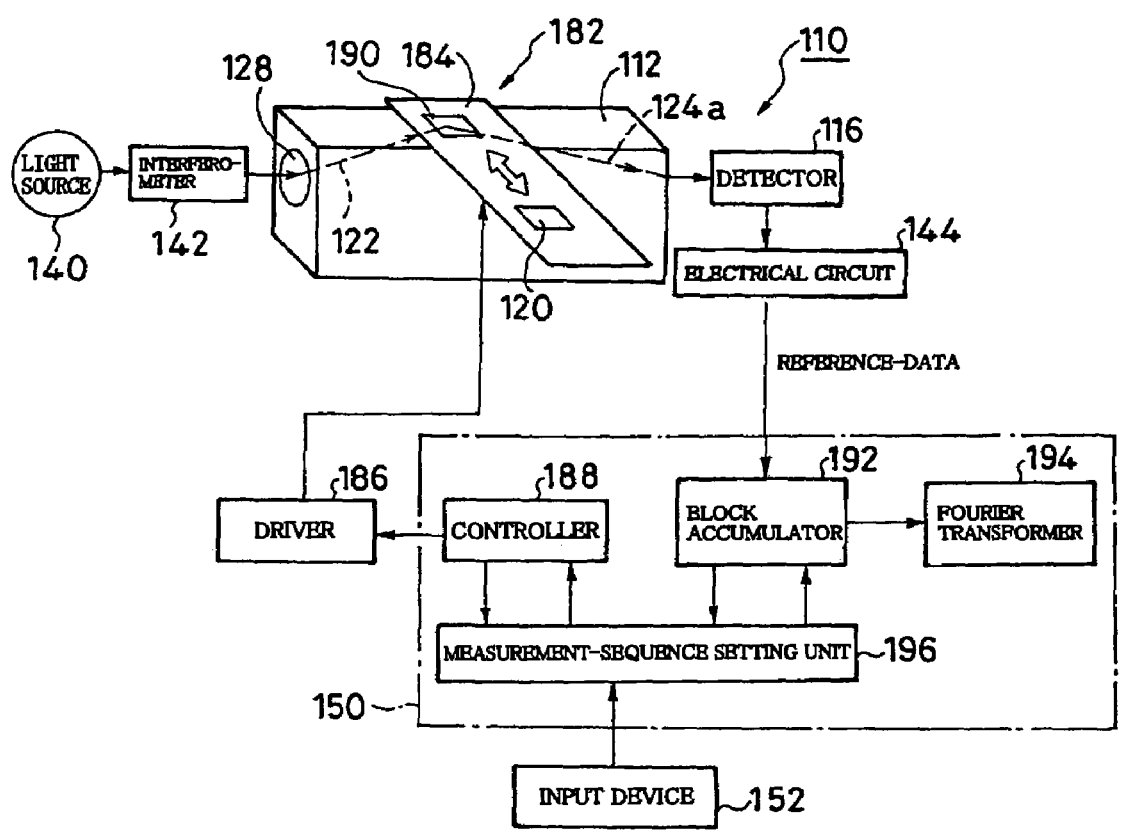
FIG. 7A and FIG. 7B are views showing an outline structure of a sample shuttle suited to a high-sensitivity reflection measurement apparatus according to another embodiment of the present invention.
Figure 7B:
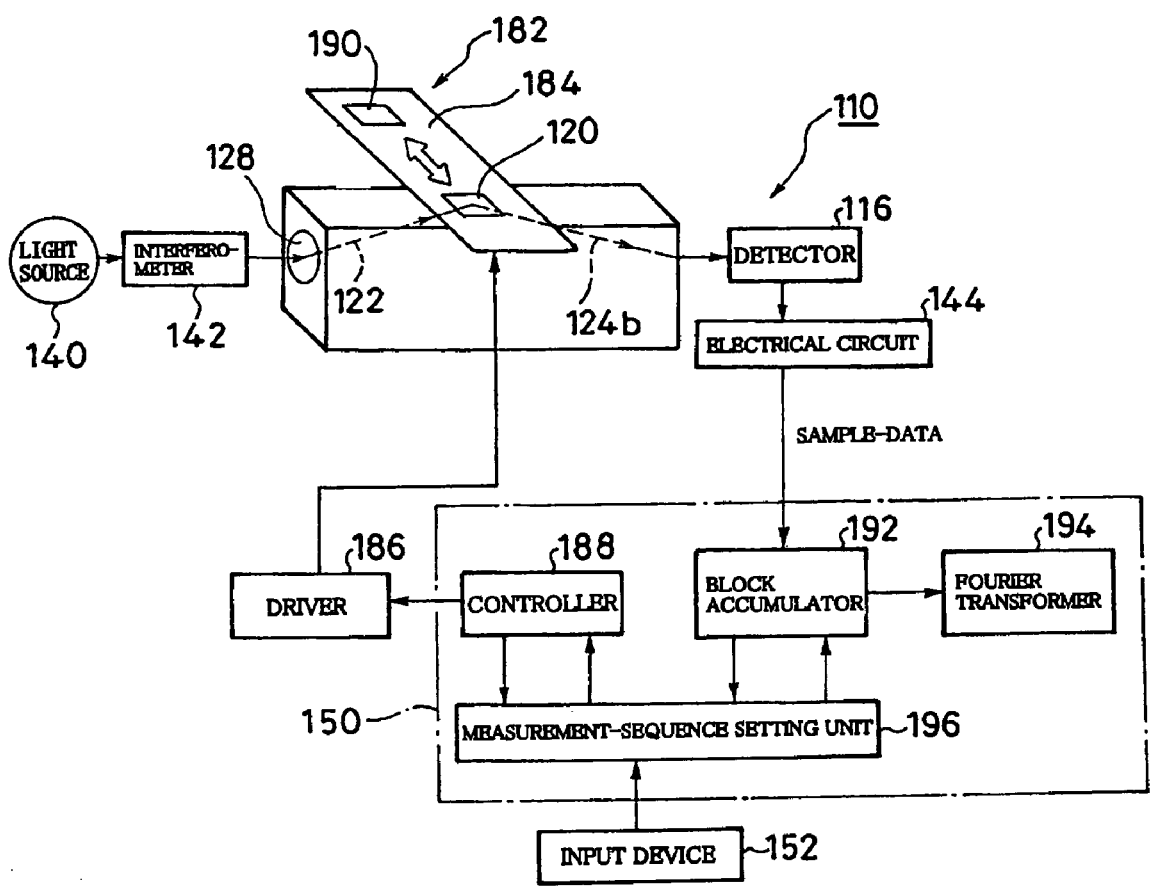

The sample shuttle will be described below by referring to FIG. 7A and FIG. 7B. FIG. 7A shows a state in a reference measurement, and FIG. 7B shows a state in a sample measurement. The same numerals as those used in FIG. 1A and FIG. 1B plus 100 are assigned to portions corresponding to those shown in FIG. 1A and FIG. 1B. A description thereof is omitted.

A sample shuttle 182 includes a sample holder 184, a driver 186, and a controller 188.

The sample shuttle 182 is disposed at the sample placement section of the high-sensitivity reflection apparatus, and alternately performs a reference measurement for a reference sample and a sample measurement for a sample under measurement.

The sample holder 184 is formed, for example, of a rectangular plate, holds a reference sample 190 and a sample 120 under measurement, and is provided so as to be able to reciprocate in directions indicated by arrows in the figures such that the reference sample 190 and the sample 120 under measurement are alternately placed in the optical path of measurement light.

The driver 186 reciprocates the sample holder 184 to alternately place the reference sample 190 and the sample 120 under measurement in the optical path of the measurement light.

The controller 188 controls the reciprocating movement of the sample holder 184 driven by the driver 186.

A computer system 150 includes a block accumulator 192, a Fourier transformer 194, and a measurement-sequence setting unit 196.

The block accumulator 192 applies block accumulation to interferogram data sent from an electrical circuit 144.

A measurement sequence input from an input device 152 is specified in the measurement-sequence setting unit 196, and includes control (switching control between the reference sample and the sample under measurement) of the reciprocating movement of the sample holder 184 driven by the driver 186 and block accumulation (switching between reference-data block accumulation and measurement-data block accumulation).

The controller 188 makes the driver 186 alternately place the reference sample 190 and the sample 120 under measurement in the optical path of the measurement light according to the measurement sequence specified in the measurement-sequence setting unit 196. With this operation, the incidence of the measurement light 122 on the reference sample 190, shown in FIG. 7A, and the incidence of the measurement light 122 on the sample 120 under measurement, shown in FIG. 7B, are alternately performed to alternately perform a reference measurement for the reference sample 190 and a sample measurement for the sample 120 under measurement.

The block accumulator 192 alternately performs interferogram block accumulation for the reference sample 190 and interferogram block accumulation for the sample 120 under measurement according to the measurement sequence specified in the measurement-sequence setting unit 196.

After the block accumulation, the Fourier transformer 194 applies a Fourier transform to each interferogram data to obtain reference spectrum data and sample spectrum data. According to the ratio of the reference spectrum data and sample spectrum data, an infrared spectrum for the sample under measurement is obtained.

In the present embodiment, sample switching performed by the sample shuttle 182 and block accumulation performed by the block accumulator 192, both according to the measurement sequence, remove an artifact caused by baseline bending or gas imbalance in the air. Therefore, a small peak can be correctly analyzed. In addition, a reference measurement for the reference sample and a sample measurement for the sample under measurement can be alternately performed by the sample shuttle 182 without opening the cover of the sample chamber. Therefore, purging-gas replacement in the sample chamber and measurement in vacuum can be easily performed.

<Optical-Element Shuttle>

In the present embodiment, an optical-element shuttle electrically driven for alternately placing an s-polarizer and a p-polarizer in an optical path is used. The optical-element shuttle is operated in synchronization with a measurement sequence to switch between a reference measurement with s-polarized light and a sample measurement with p-polarized light without breaking sample-chamber sealing and to perform block accumulation.

Figure 8A:
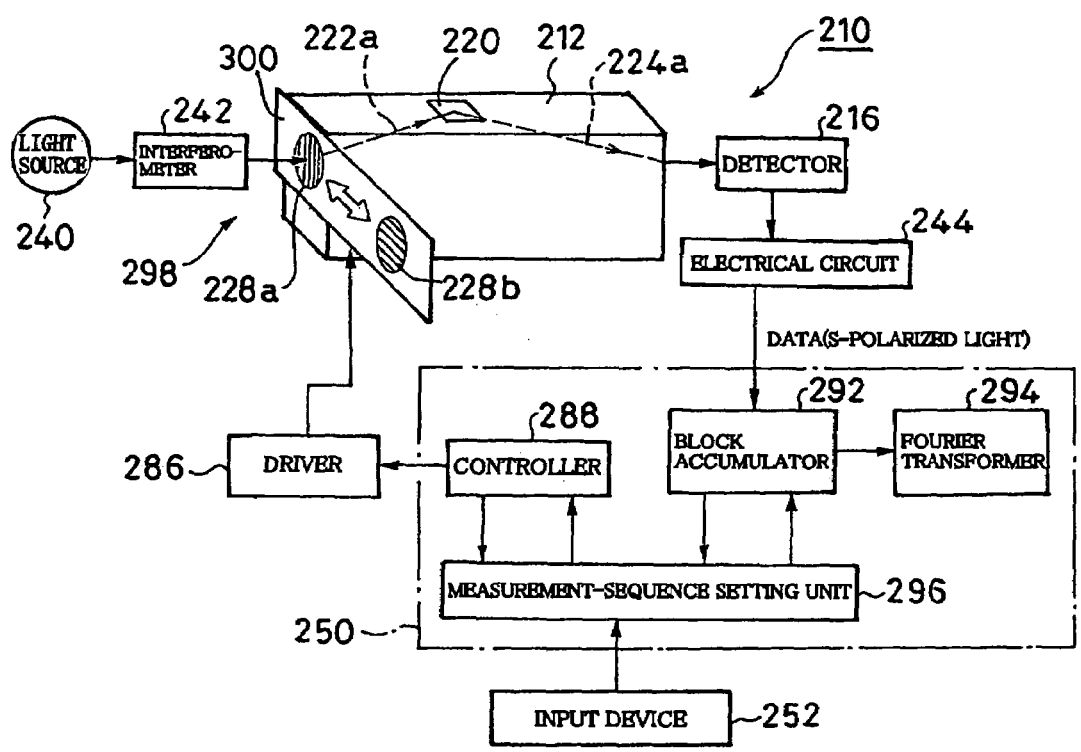
FIG. 8A and FIG. 8B are views showing an outline structure of an optical-element shuttle suited to a high-sensitivity reflection measurement apparatus according to another embodiment of the present invention.
Figure 8B:
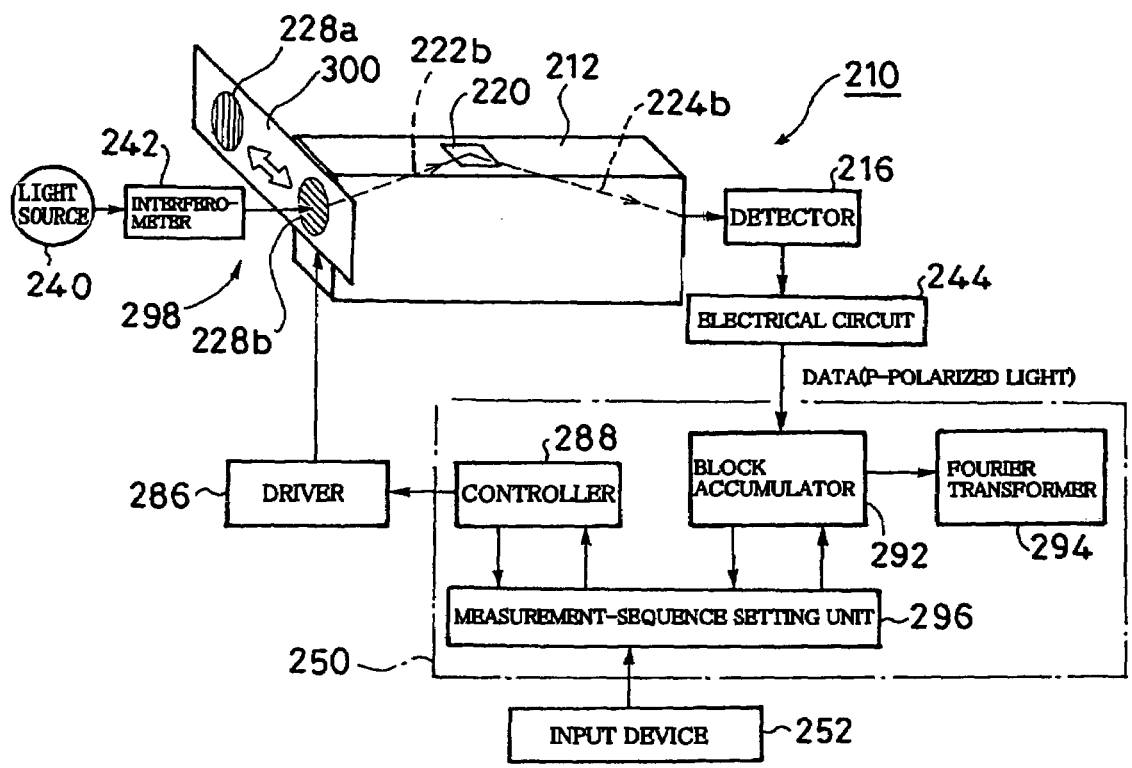

The optical-element shuttle will be described below by referring to FIG. 8A and FIG. 8B. FIG. 8A shows a state in a reference measurement, and FIG. 8B shows a state in a sample measurement. The same numerals as those used in FIG. 7A and FIG. 7B plus 100 are assigned to portions corresponding to those shown in FIG. 7A and FIG. 7B. A description thereof is omitted.

An optical-element shuttle 298 includes an s-polarizer 228a for generating s-polarized light 222a perpendicular to the plane of incidence, a p-polarizer 228b for generating p-polarized light 222b parallel to the plane of incidence, an optical-element holder 300, a driver 286, and a controller 288.

The optical-element shuttle 298 alternately performs a reference measurement with the s-polarized light 222a and a sample measurement with the p-polarized light 222b for an identical sample 220 under measurement.

The optical-element holder 300 holds the s-polarizer 228a and the p-polarizer 228b, and is provided so as to be able to reciprocate in directions indicated by arrows in the figures such that the s-polarizer 228a and the p-polarizer 228b are alternately placed in the optical path of measurement light in an FTIR apparatus.

The driver 286 reciprocates the optical-element holder 300 to alternately place the s-polarizer 228a and the p-polarizer 228b in the optical path of the measurement light in the FTIR apparatus.

The controller 288 controls the reciprocating movement of the optical-element holder 300 driven by the driver 286.

A computer system 250 includes a block accumulator 292, a Fourier transformer 294, and a measurement-sequence setting unit 296.

The block accumulator 292 applies block accumulation to interferogram data sent from an electrical circuit 244.

A measurement sequence input from an input device 252 is specified in the measurement-sequence setting unit 296, and includes control (switching control between the s-polarized light and the p-polarized light) of the reciprocating movement of the optical-element holder 300 driven by the driver 286 and block accumulation (switching between block accumulation of s-polarized-light reference data and block accumulation of p-polarized-light sample data).

The controller 288 makes the driver 286 alternately place the s-polarizer 228a and the p-polarizer 228b, both held by the optical-element holder 300, in the optical path of the measurement light in the FTIR apparatus according to the measurement sequence specified in the measurement-sequence setting unit 296. With this operation, the illumination of the s-polarized light on the sample 220 under measurement, shown in FIG. 8A, and the illumination of the p-polarized light on the sample 200 under measurement, shown in FIG. 8B, are alternately performed to alternately perform reference measurement with the s-polarized light and sample measurement with the p-polarized light.

The block accumulator 292 alternately performs block accumulation of a reference interferogram caused by the s-polarized-light illumination and block accumulation of a sample interferogram caused by the p-polarized-light illumination according to the measurement sequence specified in the measurement-sequence setting unit 296.

After the block accumulation, the Fourier transformer 294 applies a Fourier transform to each interferogram data to obtain an infrared spectrum for the sample under measurement.

In the present embodiment, switching between the s-polarized-light illumination and the p-polarized-light illumination, performed by the optical-element shuttle 298, and block accumulation of the reference data and the sample data, performed by the block accumulator 292, both according to the measurement sequence, allow even a small peak to be correctly analyzed, in the same way as with the sample shuttle. In addition, with the use of the optical-element shuttle 298, purging-gas replacement in the sample chamber and measurement in vacuum can be easily performed.

Each holder may be configured to have a circular shape and be rotated. In the embodiments described above using the holders, it is especially preferred that each holder reciprocate.

When the holder has a circular shape, a larger space is required for the holder. In addition, since measurement light is incident on a sample surface under measurement at a large angle of incidence in a high-sensitivity reflection measurement apparatus, it is difficult to arrange a holder having a circular shape. Furthermore, it is difficult to obtain good timing repeatability for placing a holder having a circular shape. Especially in the embodiments described above using the holders, since a preferable incident-side optical element has a wedge shape, it is necessary to always place the optical element in position in the optical path, which is difficult for a holder having a circular shape to achieve.

In the embodiments, each holder having a rectangular shape reciprocates, and a required space is smaller than when a holder having a circular shape is used. In addition, in the embodiments, since the plane of incidence and the plane of outgoing always form a constant angle at the incident-side optical element even when the incident-side optical element reciprocates, very good repeatability is obtained for placing the incident-side optical element in position. For these reasons, in the high-sensitivity reflection measurement apparatuses in the embodiments, it is especially preferred that the holders reciprocate as shown in FIG. 7A and FIG. 7B, and in FIG. 8A and FIG. 8B.

Figure 9A:
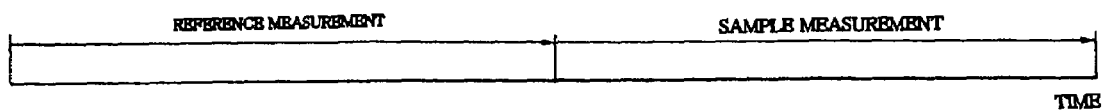
FIG. 9A and FIG. 9B are views showing measurement sequences, one of which is suited to the high-sensitivity reflection measurement apparatus shown in FIG. 7A and FIG. 7B, or in FIG. 8A and FIG. 8B.

It is generally considered that a reference measurement is first completed and then a sample measurement is performed, as shown in FIG. 9A. In this method, however, since the reference measurement and the sample measurement are performed at different times, poor measurement repeatability may occur due to a change in the measurement environment. For example, an artifact may occur due to baseline bending or gas imbalance in the air.

Figure 9B:
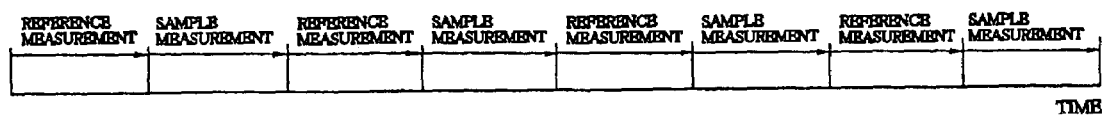

It is preferred in the above-described embodiments that a reference measurement and a sample measurement be alternately performed at short intervals according to a measurement sequence, as shown in FIG. 9B. It is also preferred that reference-data accumulation and sample-data accumulation be alternately performed in synchronization with the alternate measurements. With these operations, since the time difference between the reference measurement and the sample measurement is largely reduced, the effect of an artifact caused by baseline bending or gas imbalance in the air is largely reduced.

<Wedge-shaped Polarizer>

As described above, according to a high-sensitivity reflection measurement apparatus of the present invention, since an incident-side optical element which bends the optical path of measurement light, transmits the measurement light as linearly polarized light having a desired oscillation direction, and makes the light incident on a sample surface under measurement is provided, high-sensitivity measurements can be performed with a simple structure.

According to the present invention, since the incident-side optical element is a wedge-shaped optical element having a wire grid polarizer, higher-sensitivity measurements can be performed with a simpler structure.

According to the present invention, when an outgoing-side optical element for bending the optical path of light reflected from a sample surface under measurement and for transmitting the reflected light, a casing for accommodating the optical elements, and a sample placement section for placing a sample are provided, high-sensitivity measurements can be performed with a simpler structure.

<Light Limiter>

According to the present invention, when a light-shielding plate disposed at a certain gap with respect to a sample surface under measurement is provided and the gap is equal to a distance specified according to the size of an opening of a sample mask, higher-sensitivity measurements can be performed with a simpler structure.

According to the present invention, when a spacer having a thickness specified according to the size of the opening of the sample mask is abutted against the light-shielding plate, and the sample mask and the light-shielding plate are placed in position, a moving unit moves the light-shielding plate by a distance corresponding to the thickness of the spacer in the direction increasing the gap with respect to the sample surface under measurement. Therefore, higher-sensitivity measurements can be performed with a simpler structure.

<Sample Shuttle and Optical-Element Shuttle>

According to the present invention, a sample shuttle alternately places a sample under measurement and a reference sample in the optical path of measurement light to alternately perform a sample measurement with the sample under measurement and a reference measurement with the reference sample. Therefore, higher-sensitivity measurements can be performed with a simpler structure.

In addition, according to the present invention, an optical-element shuttle alternately makes p-polarized light and s-polarized light incident on an identical sample to alternately perform sample measurement with the p-polarized light and reference measurement with the s-polarized light. Therefore, higher-sensitivity measurements can be performed with a simpler structure.

What is claimed is:

1. A high-sensitivity reflection measurement apparatus disposed in an optical path between a light emitter and a detector of an analysis apparatus, the high-sensitivity reflection measurement apparatus comprising a single incident-side optical element, wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; and information related to the sample surface under measurement is obtained according to light reflected from the sample surface under measurement when the linearly polarized light from the incident-side optical element is incident on the sample surface under measurement.

2. A high-sensitivity reflection measurement apparatus, disposed in an optical path between a light emitter and a detector of an analysis apparatus, the high-sensitivity reflection measurement apparatus comprising an incident-side optical element, wherein the incident-side optical element has transmittance with respect to the measurement light and a higher refractive index than an atmosphere in the optical path of the measurement light, wherein the incident-side optical element is a wedge-shaped optical element having a wire grid polarizer made by providing a wire grid polarizer for making the measurement light to linearly polarized light having a desired oscillation direction, on a wedge-shaped measurement-light transmission substrate for bending the optical path of the measurement light emitted from the light emitter such that the angle of incidence of the measurement light with respect to the sample surface under measurement, after passing through the incident-side optical element, is a desired angle ranging from 70 degrees inclusive to 90 degrees exclusive, and wherein information related to the sample surface under measurement is obtained according to light reflected from the sample surface under measurement when the linearly polarized light from the incident-side optical element is incident on the sample surface under measurement.

3. A high-sensitivity reflection measurement apparatus disposed in an optical path between a light emitter and a detector of an analysis apparatus, the high-sensitivity reflection measurement apparatus comprising:

an incident-side optical element;

a wedge-shaped outgoing-side optical element for bending the optical path of the light reflected from the sample surface under measurement such that the optical path of the light reflected from the sample surface under measurement matches an optical path to the detector when the light reflected from the sample surface under measurement is transmitted;

a casing for accommodating at least the incident-side optical element and the outgoing-side optical element; and a sample placement section provided on the casing, for setting the sample; wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; wherein information related to the sample surface under measurement is obtained according to light reflected from the sample surface under measurement when the linearly polarized light from the incident-side optical element is incident on the sample surface under measurement; and wherein the incident-side optical element makes the measurement light incident on the sample surface under measurement of a sample placed at the sample placement section and the outgoing-side optical element takes out the light reflected from the sample surface under measurement.

4. A high-sensitivity reflection measurement apparatus, disposed in an optical path between a light emitter and a detector of an analysis apparatus, the high-sensitivity reflection measurement apparatus comprising:

an incident-side optical element;

a sample mask having an opening for limiting the sample surface under measurement; and a light-shielding plate disposed in the direction perpendicular to the sample surface under measurement, at a certain gap with respect to the sample surface under measurement, the gap being equal to a distance determined according to the size of the opening of the sample mask, wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; wherein information related to the sample surface under measurement is obtained according to light reflected from the sample surface under measurement when the linearly polarized light from the incident-side optical element is incident on the sample surface under measurement; and wherein the light-shielding plate takes out reflected light having reflection points of the measurement light on the sample surface under measurement limited by the opening of the sample mask and having an angle of incidence ranging from 70 degrees inclusive to 90 degrees exclusive at the reflection points, through the gap with respect to the sample surface under measurement, and blocks other unnecessary light.

5. A high-sensitivity reflection measurement apparatus disposed in an optical path between a light emitter and a detector of an analysis apparatus, the high-sensitivity reflection measurement apparatus comprising:

an incident-side optical element;

a sample mask having an opening for limiting the sample surface under measurement;

a light-shielding plate disposed in the direction perpendicular to the sample surface under measurement, at a certain gap with respect to the sample surface under measurement, the gap being equal to a distance determined according to the size of the opening of the sample mask;

a spacer disposed at the side opposite the sample surface under measurement, of the sample mask and having a thickness determined according to the size of the opening of the sample mask, and a moving unit for moving and holding the light-shielding plate at any position in the direction perpendicular to the sample surface under measurement; wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; wherein information related to the sample surface under measurement is obtained according to light reflected from the sample surface under measurement when the linearly polarized light from the incident-side optical element is incident on the sample surface under measurement, wherein the light-shielding plate takes out reflected light having reflection points of the measurement light on the sample surface under measurement limited by the opening of the sample mask and having an angle of incidence ranging from 70 degrees inclusive to 90 degrees exclusive at the reflection points, through the gap with respect to the sample surface under measurement, and blocks other unnecessary light, and wherein when the spacer for the sample mask is abutted against the light-shielding plate to place the sample mask and the light-shielding plate in position, the moving unit relatively moves the light-shielding plate by a distance corresponding to the thickness of the spacer in a direction in which the gap with respect to the sample surface under measurement increases to make the gap between the sample-surface under measurement and the light-shielding plate equal to the distance determined according to the size of the opening of the sample mask.

6. A high-sensitivity reflection measurement apparatus disposed in an optical path between a light emitter and a detector of an analysis apparatus, the high-sensitivity reflection measurement apparatus comprising:

an incident-side optical element; and a sample shuttle for alternately performing a sample measurement with a sample under measurement and a reference measurement with a reference sample, wherein the sample shuffle comprises:

a sample holder for holding the sample under measurement and the reference sample, the sample holder being provided so as to reciprocate freely in order to alternately place the sample under measurement and the reference sample in the optical path of the measurement light;

a driver for reciprocating the sample holder to alternately place the sample under measurement and the reference sample in the optical path of the measurement light;

a controller for controlling the reciprocating movement of the sample holder driven by the driver, and wherein the controller makes the driver alternately place
the sample under measurement and
the reference sample held by the sample holder
in the optical path of the measurement light according to a predetermined measurement sequence such that the measurement light is alternately incident on the sample under measurement and the reference sample to alternately perform the sample measurement and the reference measurement, wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; and wherein information related to the sample surface under measurement is obtained according to light reflected from the sample surface under measurement when the linearly polarized light from the incident-side optical element is incident on the sample surface under measurement.

7. A high-sensitivity reflection measurement apparatus disposed in an optical path between a light emitter and a detector of an analysis apparatus, the high-sensitivity reflection measurement apparatus comprising:

an incident-side optical element;

an optical-element shuttle for alternately performing a sample measurement with p-polarized light and a reference measurement with s-polarized light, for an identical sample under measurement; wherein the incident-side optical element comprises a p-polarizer for generating the p-polarized light and an s-polarizer for generating the s-polarized light; wherein the optical-element shuttle comprises:
  an optical-element holder for holding the p-polarizer and the s-polarizer, the optical-element holder being provided so as to reciprocate freely in order to alternately place the p-polarizer and the s-polarizer in the optical path of the measurement light;
  a driver for reciprocating the optical-element holder to alternately place the p-polarizer and the s-polarizer in the optical path of the measurement light; and
  a controller for controlling the reciprocating movement of the optical-element holder driven by the driver; wherein the incident-side optical element bends the optical path of measurement light emitted from the light emitter such that the angle of incidence of the measurement light emitted from the light emitter with respect to a sample surface under measurement is a desired angle ranging from 70 degrees inclusive to 90 degrees exclusive with respect to the direction perpendicular to the sample surface under measurement, transmits the measurement light as linearly polarized light having a desired oscillation direction, and makes the linearly polarized light incident on the sample surface under measurement; wherein information related to the sample surface under measurement is obtained according to light reflected from the sample surface under measurement when the linearly polarized light from the incident-side optical element is incident on the sample surface under measurement; and wherein the controller makes the driver alternately place
  the p-polarizer and
  the s-polarizer held by the optical-element holder in the optical path of the measurement light according to a predetermined measurement sequence such that the p-polarized light and the s-polarized light are alternately incident on the identical sample under measurement to alternately perform the sample measurement and the reference measurement.

\* \* \* \* \*